United States Patent [19]

Garces et al.

[11] Patent Number: 4,657,890
[45] Date of Patent: Apr. 14, 1987

[54] CATALYST FOR PREPARING P-ISOPROPENYL PHENOL

[75] Inventors: Juan M. Garces, Midland, Mich.; John W. Robinson, Lake Jackson, Tex.

[73] Assignee: The Dow Chemical Company, Midland, Mich.

[21] Appl. No.: 778,040

[22] Filed: Sep. 20, 1985

[51] Int. Cl.$^4$ .......................... B01J 21/06; B01J 23/02; B01J 23/06; B01J 23/10

[52] U.S. Cl. .................................. 502/340; 502/303; 502/324; 502/343; 502/344; 568/806

[58] Field of Search ............... 502/303, 324, 340, 343, 502/344; 568/806

[56] References Cited

U.S. PATENT DOCUMENTS

| | | | |
|---|---|---|---|
| 1,798,813 | 3/1931 | Schoeller et al. | 568/781 |
| 2,434,418 | 1/1948 | La Lande | 23/110 |
| 2,497,503 | 2/1950 | Jones | 260/621 |
| 3,576,891 | 4/1971 | Rosenthal | 260/643 |
| 4,054,611 | 10/1977 | Mimaki et al. | 260/626 R |
| 4,131,749 | 12/1978 | Kiedik et al. | 568/806 |
| 4,227,012 | 10/1980 | Suid et al. | 560/131 |
| 4,242,528 | 12/1980 | Kato et al. | 568/781 |
| 4,245,128 | 1/1981 | Kato et al. | 568/806 |
| 4,258,221 | 3/1981 | Knudsen et al. | 568/806 |
| 4,450,310 | 5/1984 | Fox et al. | 585/400 |
| 4,594,459 | 6/1986 | Inoue | 568/781 |

FOREIGN PATENT DOCUMENTS 905994 9/1962 United Kingdom .

Primary Examiner—W. J. Shine
Attorney, Agent, or Firm—P. D. Hayhurst; M. F. Zuckerman

[57] ABSTRACT

An improved alkaline catalyst which is especially useful in the preparation of alpha-alkenyl aromatic compounds, such as p-isopropenylphenol, via the cleavage of cleavable organic compounds, e.g., dihydroxydiaryl alkanes such as bisphenol A.

18 Claims, No Drawings

CATALYST FOR PREPARING P-ISOPROPENYL PHENOL

BACKGROUND OF THE INVENTION

This invention relates to a process for producing alkenyl aromatic compounds. More particularly, it relates to a process for cleaving certain diphenyl alkanes, and an improved catalyst therefor.

It is well-known that dihydroxy diphenyl alkanes can be cleaved by heating them in the presence of an alkaline catalyst to give phenol and alkenyl phenols, and several methods have been proposed for this cleavage reaction. For example, U.K. Pat. No. 905,994 teaches the use of basic catalysts such as alkali metals or alkaline earth metals or the oxides, hydroxides, alcoholates, phenolates, alkyl-carboxylates, carbonates, amides and hydrides thereof, as well as aluminum, zinc, cadmium and lead, or the above-mentioned compounds of these metals in a process for the production of alpha-alkenyl, alpha-cycloalkenyl and alpha-aralkenyl phenols. Other known methods for the preparation of alpha-alkenyl phenols are disclosed in U.S. Pat. No. 4,054,611; U.S. Pat. No. 4,242,528; U.S. Pat. No. 4,245,128; U.S. Pat. No. 2,497,503; and U.S. Pat No. 1,798,813. The latter patent discloses that compounds such as 4-isopropylene phenol can be prepared by thermally cleaving dihydroxydiaryl alkanes in the presence of a surface catalyst, such as magnesium aluminum hydrosilicates, fuller's earth, silica gel, active carbon and similar porous bodies. However, the majority of said patents employ simple catalysts such as sodium hydroxide, potassium hydroxide, or the alkali metal salts of bisphenol A. Scuh catalysts are disadvantageous in that they produce relatively large amounts of polymers and tars which reduce the yield of the desired compounds.

U.S. Pat. No. 3,576,891 discloses a supported alkali metal hydroxide catalyst for the removal of esters and acids from t-butyl alcohol. It is taught that the alkali metal hydroxide is supported on an inert support such as magnesia. The final catalyst composition is taught to contain from about 5 weight percent to 30 weight percent alkali metal hydroxide.

U.S. Pat. No. 4,450,310 discloses catalysts comprising the mixed oxide of alkali metal and alkaline earth metals. Said catalysts are prepared by calcination in air of compounds of said metals, examples of suitable ions being carbonates, hydroxides, halides or salts of organic or inorganic acids. Said patent discloses the use of these catalysts for the conversion of methane to olefins and hydrogen. Said catalysts may optionally contain promoters such as rhodium, copper, rhenium, tungsten, zirconium, and mixtures thereof. The preparation of said catalysts is disadvantageous in that calcination at very high temperatures is required.

In view of the deficiencies of the prior art, it would be desirable to have a supported catalyst having a small percentage of alkali metal, which could be easily prepared, and which could be employed advantageously for the cleavage of dihydroxydiaryl alkanes.

SUMMARY OF THE INVENTION

The catalyst of the present invention is such a catalyst, and has the general formula $[AO_x]_{1-y}[A(OH)_n]_y[Z_2O]_z \cdot qH_2O$ wherein A is a metal of Group IIA, IIB, IIIB, IVA, IVB, or VIIB; Z is an alkali metal; n and x are numbers sufficient to satisfy the valence of A; q is a non-negative number; z is greater than zero, and y is a positive number $\leq 1$, with the proviso that the ratio y/z is from about 10 to about 80. Said catalysts are useful for disproportionating $H_2S$ into sulfur and hydrogen, for the preparation of tetramethyldihydropyridine from acetone and ammonia, and for other processes in which a basic or alkaline catalyst is advantageously employed. The catalysts are especially useful in the cleavage of dihydroxydiaryl alkanes to form the corresponding alkenyl hydroxyaryl compounds, giving, e.g., high yields of isopropenylphenol from bisphenol A with unexpectedly high selectivity to the monomer and relatively low selectivity to polymeric residues. Surprisingly, the catalyst is effective with very low levels of alkali metal hydroxides.

DETAILED DESCRIPTION OF THE INVENTION

The preferred process for the preparation of the catalyst of the present invention basically involves contacting a solution of an alkali metal hydroxide with a metal oxide support component under reaction conditions, followed by recovery of the catalyst. The alkali metal hydroxide solution is prepared using known techniques. Typically, the solvent is employed in an amount sufficient to dissolve the alkali metal hydroxide. Preferred alkali metal hydroxides include lithium, sodium, potassium, rubidium and cesium. The most preferred alkali metal hydroxide is potassium hydroxide. Mixed alkali metal hydroxides can be employed if desired. The solvent can be any material which solubilizes an alkali metal hydroxide. Examples of typical solvents include water, methanol, ethanol, and other polar solvents. Water is the preferred solvent. Desirably, the concentration of the alkali metal hydroxide in the solvent ranges from about 0.01M to about 5M and preferably ranges from about 0.1M to about 1M.

The metal oxide support component desirably is an oxide of a metal of Group IIA, IIB, IIIB, IVA, IVB, or VIIB. The metal oxide support component can be prepared using known methods, although it is preferred that the metal oxide support component be substantially free of halides. Desirably, the metal oxide support component has a surface area greater than about 10 $m^2/g$. Preferably, the support component has a surface area of from about 50 to about 500 $m^2/g$. Examples of preferred metal oxides include oxides of magnesium, calcium strontium, barium, lanthanum, titanium, zirconium, zinc, tin, and manganese, with magnesium being the most preferred.

Advantageously, the molar ratio of the metal of the support component to the alkali metal ranges from about 10 to about 80. Preferably, this ratio ranges from about 20 to about 40. These ratios govern the amount of solution to be contacted with the metal oxide support component, as discussed hereinbelow. Most preferably, the catalyst contains less than 5 weight percent alkali metal hydroxide.

In the preferred method for the preparation of the catalyst of the present invention, the solution of the alkali metal hydroxide is contacted with the metal oxide support component, preferably with stirring, to form a slurry. The slurry preferably is stirred for a period of time sufficient to result in the formation of a smooth paste. Typically, the end of the time period is signaled by a cease in the end of thermic reaction which occurs during the contacting step. Preferably, the smooth paste is filtered to give a filter cake. The filter cake preferably is not washed.

The filter cake is dried in air under conditions sufficient to drive off excess solvent. The dried filter cake can be ground to form the catalyst of the present invention. The preceding stirring, filtering and drying steps can be performed using techniques well-known in the art.

The catalyst of the present invention is represented generally by the formula $[AO_x]_{1-y}[A(OH)_n]_y[Z_2O]_z \cdot q H_2O$ wherein A is a metal of Group IIA, IIB, IIIB, IVA, IVB, or VIIB; Z is an alkali metal; n and x are numbers sufficient to satisfy the valence of A; q is a non-negative number; z is greater than zero, and y is a positive number $\leq 1$, with the proviso that the ratio y/z is from about 10 to about 80, i.e., the ratio of the metal of the metal oxide support to the metal of the alkali metal hydroxide is from about 10 to about 80 moles per mole. Preferably, q=z. Typically, the alkali metal hydroxide solution contains an excess of alkali metal hydroxide, as all of the alkali metal hydroxide typically is not incorporated into the final catalyst, i.e., some of the alkali metal hydroxide is filtered off with the excess solvent during the filtering step. The amount of solution to employ to achieve a given metal to metal ratio is easily determined by routine experimentation. Analysis of the filtrate solution for alkali metal content gives, by difference, the amount of alkali metal remaining in the catalyst.

Typically, the surface area of the catalyst of the present invention ranges from about 10 to about 500 m$^2$/g. Preferably, the surface area ranges from about 20 to about 200 m$^2$/g.

The catalyst of the present invention is useful in processes wherein an alkaline catalyst can be employed. The catalyst is especially useful in the cleavage of dihydroxydiaryl alkanes to form the corresponding alkenyl aryl compounds. The catalysts of the present invention can be substituted in known processes advantageously. For example, the catalyst of the present invention can be substituted into the processes described in U.S. Pat. No. 1,798,813; U.S. Pat. No. 2,497,503; U.S. Pat. No. 4,242,528; U.S. Pat. No. 4,245,128; U.S. Pat. No. 4,054,611; and U.K. Pat. No. 905,994. The teachings of these patents regarding cleavage of organic materials are incorporated herein by reference. Additionally, the cleavable compounds of U.S. Pat. No. 4,258,221 can be used in the cleavage process of the present invention, and the teaching of said patent with respect to said compounds is incorporated herein by reference.

Cleavable organic materials suitable for use in the process of the present invention include substituted aromatic compounds having an optionally substituted aliphatic bridging moiety containing from 2 to about 7 carbon atoms. The cleavable organic compound contains at least one electron-withdrawing or electron-donating moiety as a substituent on at least one of the aromatic moieties of the compound. Examples of typical cleavable organic compounds include 2,4'-(1-methylethylidene)bisphenol and 1,1-bis(4-hydroxyphenyl)cyclohexane. Additional examples are listed in U.S. Pat. No. 4,245,128; and the teachings of said patent relating to cleavable organic aromatic compounds are incorporated herein by reference. Preferred organic compounds suitable for cleaving are represented generally by the formula:

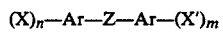

wherein each Ar independently is an aromatic moiety, Z is an optionally substituted aliphatic moiety having from 2 to about 7 carbon atoms, X and X' are independently electron-withdrawing or electron-donating moieties, and n and m are integers, with the proviso that the quantity (m+n) is greater than zero. Typical examples of X and X' include —R, —OR, —NRR', halo, —NO$_2$, —SO$_3$R and —COOR, wherein R and R' are independently hydrogen, alkyl, aralkyl or aryl, with the proviso that all occurrences of X and X' cannot be hydrogen. Preferably, X and X' are —OH and each Ar is phenyl. More preferred compounds are represented by the formula:

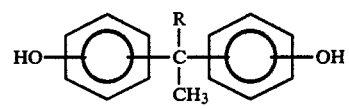

wherein R preferably is hydrogen or alkyl of 1 to about 3 carbon atoms. Most preferably, R is methyl, and the hydroxyl groups are in the para positions, i.e., 2,2-bis(4-hydroxyphenyl)propane, or bisphenol A, is the most preferred organic compound to be cleaved.

A catalytic amount of the catalyst advantageously is employed. Typically, from about 0.001 to about 10 weight parts catalyst are employed per weight part of cleavable organic compound. Preferably, from about 0.5 to about 5 weight parts of catalyst are employed. The catalyst can be employed, e.g., in a fixed catalyst bed, and the process can be conducted continuously or batchwise.

SPECIFIC EMBODIMENTS

The following preparation and examples are provided for illustrative purposes only and are not intended to limit the scope of the invention or claims. All parts and percentages are by weight unless otherwise specified.

EXAMPLE 1

Preparation of Modified Magnesium Oxide Catalyst

One mole of alkali metal hydroxide (66 g of 85 weight percent KOH, the remaining 15 weight percent being water) is mixed with enough water to make a 1000-ml solution. This solution is added at room temperature to 500 g of MAGOX Premium Grade magnesium oxide (available from Basic Chemicals Division of Basic, Inc.), having a surface area of about 100 m$^2$/g. A typical chemical analysis of MAGOX Premium Grade gives the following values, on a loss-free basis: MgO-97.5; CaO-1.00; SiO$_2$-0.75; Fe$_2$O$_3$-0.15; Al$_2$O$_3$-0.25. MAGOX Premium Grade has a median particle size less than 2 microns, and a crystallite size of about 600 angstroms as measured by X-ray line broadening. The resulting mixture is stirred for approximately one hour to obtain a smooth paste. The reaction is exothermic.

| Temperature (°C.) | Time (min) |
|---|---|
| 40 | 0 |
| 45 | 5 |
| 60 | 20 |
| 80 | 25 |
| 100 | 30 |
| 100 | 35 |

| Temperature (°C.) | Time (min) |
|---|---|
| 95 | 40 |
| 95 | 50 |
| 95 | 60 |

The paste is filtered in a Buchner funnel, and is not washed. The filter cake is transferred to glass trays and is spread to a thickness of approximately ½ inch. The glass trays containing the ½-inch thick cake are placed in an air circulating oven for about 2 hours at about 110° C. to dry the cake. The dried cake is ground and is stored for later use. The catalyst has a surface area of approximately 50 m²/g and contains about one milliequivalent of KOH per gram of MAGOX Premium Grade MgO. This material is employed as modified magnesium oxide catalyst.

EXAMPLES 2-9

The procedure of Example 1 is repeated except that the following metal oxides are employed, respectively, for each example:

| Ex. | Metal Oxide |
|---|---|
| 2 | ZnO |
| 3 | MnO |
| 4 | $ZrO_2$ |
| 5 | $LaO_3$ |
| 6 | $TiO_2$ |
| 7 | CaO |
| 8 | BaO |
| 9 | $SnO_2$ |

Some of the catalysts described in the prior art require calcination at high temperatures and use raw materials when upon decomposition produced acid or reactive vapors. The compositions of the present invention are produced under very mild conditions in such a way that only ordinary equipment is required for their production. The catalysts of the present invention are made from compounds that do not require specific precautions for handling (just those normally used for handling strong alkaline materials) and do not produce acid or reactive vapors. In fact, only water is removed from the catalysis in the activation procedure.

General Cleavage Reaction Procedure

A sample of bisphenol A is added to a reaction vessel equipped with a heating means and a means for continuous removal of vaporized reaction products. The reaction vessel is evacuated to a pressure of 50 mm mercury. The heaing means is controlled by means of a rheostat which is set at 75 on a scale of 140. The vessel is heated to a temperature of 160° C. A stirring means is activated when the bisphenol melts. Vaporized reaction products begin to exit the vessel at a temperature of 210° C. The temperature in the reaction vessel continues to rise until it reaches 230° C.-235° C., at which point it remains essentially constant for the majority of the remainder of the reaction. The temperature in the vessel is allowed to reach 260° C., at which time the overhead temperature rapidly drops, as no more product is being produced. The product is analyzed using liquid chromatography.

In this procedure, an ice water bath is employed to quench the hot liquid p-isopropenylphenol product in order to minimize the oligomerization that would otherwise occur in the product receiving vessel.

The General Cleavage Reaction Procedure is employed using approximately 1 part of catalyst per 100 parts of PARABIS ® brand resin intermediate. PARABIS ®, which is mainly bisphenol A, is a trademark of The Dow Chemical Company. The procedure is repeated using each of the catalysts of Examples 1-9. The results are summarized in Table I.

TABLE I
Summary of KOH-Modified Catalyst Study

| Ex. | Catalyst | Product Composition, Wt. % | | | | | % Recovery | Temp. °C. | | Run Time (Hours) |
|---|---|---|---|---|---|---|---|---|---|---|
| | | Phenol | IPP | Dimer | Bisphenol | Total | | Bottom | Ovhd | |
| 1 | MgO | 42.8 | 20.7 | 9.25 | 10.8 | 83.5 | 97 | 269 | 120 | 1.3 |
| 2 | ZnO | 30.4 | 7.25 | 29.4 | 4.3 | 71.35 | 96 | 275 | 116 | 1.9 |
| 3 | MnO | 36.8 | 11.3 | 9.68 | 16.6 | 74.4 | 97 | 275 | 116 | 1.6 |
| 4 | $ZrO_2$ | 41.8 | 11.4 | 22.8 | 9.3 | 85.3 | 96 | 270 | 115 | 1.6 |
| 5 | $La_2O_3$ | 44.1 | 11.3 | 12.4 | 6.43 | 74.2 | 98 | 275 | 110 | 1.9 |
| 6 | $TiO_2$ | 47.8 | 23.4 | 2.65 | 2.97 | 76.8 | 92 | 265 | 100 | 1.9 |
| 7 | CaO | 49.1 | 15.8 | 7.12 | 3.4 | 75.4 | 97 | 228 | 110 | 1.3 |
| 8 | BaO | 45.1 | 20.1 | 4.7 | 2.19 | 72.1 | 100 | 265 | 145 | 1.3 |
| 9 | $SnO_2$ | 35.5 | 20.2 | 1.53 | 9.19 | 66.4 | 98 | 265 | 132 | 1.4 |

Pressure maintained constant at 50 mm Hg abs.

In Table I the "% Recovery" column indicates the percent of the initial organic feed which is recovered overhead. Higher numbers indicate that fewer undesirable "heavies" are formed. A relatively shorter Run Time indicates higher catalytic activity. Temperatures are steady state temperatures. Lower overhead temperature indicates that relatively more phenol is being produced, while a higher overhead temperature indicates that the overhead stream has a relatively higher boiling point.

EXAMPLES 10-13

The procedure of Example 1 is repeated on a smaller scale using 50 g of MAGOX Premium Grade and 100 ml of one molar aqueous solutions of lithium hydroxide, sodium hydroxide, potassium hydroxide and cesium hydroxide, respectively. The dried solids have the following characteristics:

| Example | Catalyst Surface Area (m²/g) | meq Metal Hydroxide per g MgO | Catalyst Composition |
|---|---|---|---|
| 10 | 83 | 1.1 | LiOH/MgO |
| 11 | 19 | 1.0 | NaOH/MgO |
| 12 | 52 | 1.0 | KOH/MgO |
| 13 | 23 | 1.0 | CsOH/MgO |

COMPARATIVE CATALYSTS 1-3

(See Table II)

The catalyst of Comparative Experiment 1 is unmodified MAGOX Premium Grade MgO which is ground into a fine powder before use.

The catalyst of Comparative Experiment 2 is unmodified reagent grade NaOH which is ground into a fine powder before use.

The catalyst of Comparative Experiment 3 is unmodified reagent grade KOH which is ground into a fine powder before use.

The Comparative catalysts and the catalyst of Example 10 are employed in The General Cleavage Reaction Procedure with exceptions indicated. The results are summarized in Table II.

TABLE II

|  | Catalyst | | | |
| --- | --- | --- | --- | --- |
|  | MgO Comp. 1 | NaOH Comp. 2 | KOH Comp. 3 | Mod. MgO Ex. 10 |
| Pressure (mm Hg) | 50 | 15 | 15 | 50 |
| Charge (g of Parabis ®) | 598 | 630 | 500 | 659 |
| Catalyst (% of total charge) | 1.0 | 1.0 | 2.0 | 0.5 |
| Temperature reaction started (°C.) | 255 | 176 | 168 | 210 |
| Reaction rate (g/minute) | very slow | 4.0 | 3.9 | 5.3 |
| % Recovery* | <5 | 91.1 | 87.2 | 98.5 |
| % 4,4-isopropylidenediphenol in overhead material (wt. %) | — | 2.50±1.0 | 2.50±1.0 | 4.75±1.0 |

*% Recovery = overhead material/charge × 100

What is claimed is:

1. A catalyst composition of the formula $[AO_x]_{1-y}[A(OH)_n]_y[Z_2O]_z \cdot qH_2O$ wherein A is a metal of Group IIA, IIB, IIIB, IVA, IVB or VIIB; $[AO_x]_{1-y}$ is a metal oxide support component; Z is an alkali metal; n and x are numbers sufficient to satisfy the valence of A; q is a non-negative number; z is greater than zero, and y is a positive number $\leq 1$, with the proviso that said catalyst composition contains less than about 5 weight percent alkali metal hydroxide.

2. A composition of claim 1 wherein Z comprises at least one of Li, Na, K, Rb or Cs.

3. A composition of claim 2 wherein A is a metal of Group IIA or Group IVB.

4. A composition of claim 3 wherein the surface area of the metal oxide support component of the catalyst is greater than about 10 m$^2$/g.

5. A composition of claim 1 wherein q=z.

6. A composition of claim 3 wherein A is Mg, Ca, Sr or Ba.

7. A composition of claim 6 wherein the surface area is from about 10 to about 500 m$^2$/g.

8. A composition of claim 6 wherein A is Mg and Z is K.

9. A catalyst of claim 8 wherein the surface area is from about 20 to about 200 m$^2$/g.

10. A catalyst composition of the formula $[AO_x]_{1-y}[A(OH)_n]_y[Z_2O]_z \cdot qH_2O$ wherein A is magnesium, calcium, barium, lanthanum, titanium, zirconium, zinc, tin or manganese; $[AO_x]_{1-y}$ is a metal oxide support component; Z is an alkali metal; n and x are numbers sufficient to satisfy the valence of A; q is a non-negative number; z is greater than zero; and y is a positive number $\leq 1$, with the proviso that said catalyst composition contains less than about 5 weight percent alkali metal hydroxide.

11. A composition of claim 10 wherein Z comprises at least one of Li, Na, K, Rb or Cs.

12. A catalyst of claim 10 wherein A is Ba, Ca, Sn or Mg.

13. A catalyst of claim 11 wherein A is Mg.

14. A catalyst of claim 13 wherein Z is K.

15. A catalyst of claim 14 wherein the metal oxide support component comprises about 97.5% magnesium oxide with a surface area of about 100 m$^2$/g., a median particle size less than 2 microns, and a crystallite size of about 600 angstroms as measured by X-ray line broadening.

16. A composition of claim 6 wherein A is Mg and Z is Li.

17. A composition of claim 6 wherein A is Mg and Z is Na.

18. A composition of claim 11 wherein A is magnesium and Z is Li.

* * * * *